(12) United States Patent
Blaschke et al.

(10) Patent No.: US 7,198,150 B1
(45) Date of Patent: Apr. 3, 2007

(54) DEVICE AND METHOD FOR HYDRATING AND REHYDRATING ORTHOPEDIC GRAFT MATERIALS

(75) Inventors: R. Craig Blaschke, Leesburg, IN (US); Daniel B Smith, Warsaw, IN (US); Gene H Hawkins, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 356 days.

(21) Appl. No.: 10/686,445

(22) Filed: Oct. 15, 2003

Related U.S. Application Data

(63) Continuation-in-part of application No. 09/908,151, filed on Jul. 18, 2001, now Pat. No. 6,648,133.

(51) Int. Cl.
B65D 25/08 (2006.01)

(52) U.S. Cl. ............... 206/221; 206/364; 206/438; 206/524.8

(58) Field of Classification Search ............... 206/219, 206/221, 364, 368, 438, 524.8; 604/410, 604/416
See application file for complete search history.

(56) References Cited

U.S. PATENT DOCUMENTS

| | | | |
|---|---|---|---|
| 3,074,544 A | | 1/1963 | Bollmeier et al. |
| 3,082,867 A | * | 3/1963 | Gelpey .................. 206/221 |
| 3,294,227 A | | 12/1966 | Schneider et al. |
| 3,608,709 A | | 9/1971 | Pike |
| 4,463,875 A | | 8/1984 | Tepic |
| 4,467,588 A | | 8/1984 | Carveth |
| 4,878,903 A | * | 11/1989 | Mueller .................. 206/364 |
| 4,994,056 A | * | 2/1991 | Ikeda ..................... 206/221 |
| 5,045,065 A | * | 9/1991 | Raulerson ............... 604/158 |
| 5,114,004 A | * | 5/1992 | Isono et al. ............. 206/222 |
| 5,370,221 A | | 12/1994 | Magnusson et al. |
| 5,398,483 A | | 3/1995 | Smith et al. |
| 5,501,520 A | | 3/1996 | Lidgren et al. |
| 5,588,745 A | | 12/1996 | Tanaka et al. |
| 5,934,803 A | | 8/1999 | Hutter |
| 5,997,544 A | | 12/1999 | Nies et al. |
| 6,073,759 A | | 6/2000 | Lamborne et al. |
| 6,083,229 A | | 7/2000 | Constantz et al. |
| 6,149,655 A | | 11/2000 | Constantz et al. |
| 6,286,670 B1 | | 9/2001 | Smith |

* cited by examiner

*Primary Examiner*—Luan K. Bui
(74) *Attorney, Agent, or Firm*—Harness, Dickey & Pierce, P.L.C.

(57) ABSTRACT

A vacuum package system for hydrating and/or rehydrating orthopedic graft materials, such as allograft materials, xenograft materials, and synthetic materials, is described. The system primarily includes a container, which includes a dividing device for dividing the container into first and second compartments and for isolating the compartments from one another, the first compartment containing a liquid component and the second compartment containing either dry porous and/or dehydrated orthopedic graft material under vacuum with a tubular member. The elongated tubular member extends from, and is in communication with, the second compartment. The tubular portion defines vacuum reservoir device is disposed within the first compartment and is in communication with the second compartment. The vacuum reservoir device is capable of taking up substantially all residual interstitial gases and thereby ensuring thorough infusion of the liquid component into the orthopedic graft material component upon release of the dividing device so as to form either a hydrated and/or rehydrated orthopedic graft material. An optional gas permeable but liquid impermeable membrane is disposed between the second compartment and the pocket portion.

16 Claims, 9 Drawing Sheets

DEVICE AND METHOD FOR HYDRATING AND REHYDRATING ORTHOPEDIC GRAFT MATERIALS

CROSS-REFERENCE TO RELATED APPLICATIONS

This application is a continuation-in-part application of U.S. patent application Ser. No. 09/908,151, filed on Jul. 18, 2001 and issued Nov. 18, 2003 as U.S. Pat. No. 6,648,133. The disclosure of the above application is incorporated herein by reference.

FIELD OF THE INVENTION

The present invention relates generally to orthopedic materials and packaging therefor, and more particularly to a device and method for hydrating and/or rehydrating orthopedic graft materials, such as allograft materials, xenograft materials, and synthetic materials. Specifically, a vacuum package system is provided for dehydrated, e.g., freeze-dried, orthopedic graft materials, as well as dry porous orthopedic graft materials, e.g., calcium-phosphate-based materials, which allows for liquid materials to rapidly and thoroughly infuse within the pores of either type of orthopedic graft material so as to form hydrated and/or rehydrated orthopedic graft materials.

BACKGROUND OF THE INVENTION

Allografting is one of the most widely used orthopedic transplantation techniques currently being used by orthopedic surgeons. Its main use is in the field of revision joint replacement, particularly total hip replacement, although its use is also widespread in the treatment of many different types of bone defects as well.

An allograft is generally defined as a graft of tissue, such as bone tissue, from a donor of one species and grafted into a recipient of the same species. Allograft tissue is typically derived from cadaveric donors (i.e., from deceased donors). One type of allograft tissue is generally referred to as structural allograft tissue, which typically consist of blocks of bone or other types of tissue that can fastened adjacent to or onto one or more surfaces of the bone defect. These blocks can also act as bulk supports to orthopedic prostheses or other types of graft tissue. These blocks can be shaped into any number of appropriate shapes and configurations in order to suit the particular clinical needs of the patient.

In order to preserve the useful shelf life of allograft tissue, as well as to inhibit bacterial growth within the allograft tissue, it is becoming common practice to dehydrate the allograft tissue, especially by freeze-drying. Freeze-drying quickly removes virtually all of the moisture within the allograft tissue, thus inhibiting any subsequent bacterial growth. However, prior to employing the allograft tissue in a surgical setting, it is generally necessary to re-hydrate the freeze-dried allograft tissue with some sort of fluid, such as sterilized water, saline, or the like.

Typically, the freeze-dried allograft tissue is removed from its protective packaging and either introduced into a liquid source or the liquid source is introduced onto the freeze-dried allograft tissue. This is a cumbersome and sometimes sloppy process that unnecessarily exposes the freeze-dried allograft tissue to atmospheric pathogens during the rehydration process. Additionally, this haphazard process does not ensure that the liquid material will thoroughly infuse into the pores of the allograft tissue.

Additionally, xenograft materials (e.g., non-human or animal-based graft materials) as well as synthetic materials (e.g., ceramic graft materials such as calcium-based materials, calcium-phosphate-based materials, calcium-sulfate-based materials, calcium-sodium-phosphate-based materials, as well as many others) have been used as orthopedic graft materials as well. However, these materials, must also be either rehydrated, in the case of dehydrated xenografts, or hydrated in the case of dry porous synthetic materials. Therefore, the same general problems described above are also encountered with these materials as well.

Therefore, there still exists a need for an apparatus and method for either hydrating dry porous orthopedic graft materials or rehydrating dehydrated orthopedic graft materials such that the respective orthopedic graft materials can be either hydrated and/or rehydrated in a sterile, efficient, and cost-effective manner.

SUMMARY OF THE INVENTION

In accordance with one embodiment of the present invention, a container for storing and rehydrating orthopedic materials is disclosed. The container is fluidly divided by a clamping mechanism to form a first and second cavity. Disposed within and under a vacuum in the first cavity is a syringe that contains the orthopedic material. The syringe body functions as a vacuum reservoir to pull fluid from the second cavity into the first cavity. This fluid rehydrates the orthopedic material.

In another embodiment of the invention, a container is provided which has first and second chambers. Disposed between the chambers is a cylindrical member which holds orthopedic materials. The cylinder functions as a vacuum reservoir. A clamp is provided which separates liquid stored in the second chamber from the cylinder. Upon release of the clamp, the fluid flows from the second chamber into the orthopedic material.

Further disclosed is a method for reconstituting an orthopedic material. The method has the steps of providing a container which has first and second cavities. Disposing a cylindrical member between the first and second cavities so as to fluidly couple the cavities. The cylindrical member having biological materials disposed therein. Separating the cylinder from the first cavity. Applying a vacuum to the second cavity, and filling the first cavity with a liquid. The first cavity is then fluidly coupled to the cylindrical member whereupon the liquid rapidly migrates into the cylindrical member and thoroughly infuses into the orthopedic graft material so as to form a hydrated orthopedic a graft material.

A more complete appreciation of the present invention and its scope can be obtained from the following detailed description of the invention, the drawings, and the appended claims.

BRIEF DESCRIPTION OF THE DRAWINGS

The present invention will become more fully understood from the detailed description and the accompanying drawings, wherein.

The same reference numerals refer to the same parts throughout the various Figures.

DETAILED DESCRIPTION OF THE INVENTION

The present invention is useful for the hydration and rehydration of any number of different orthopedic graft materials, such as but not limited to allograft materials (e.g., human-based graft materials), xenograft materials (e.g., non-human or animal-based graft materials), and synthetic materials (e.g., ceramic graft materials such as calcium-based materials, calcium-phosphate-based materials, calcium-sulfate-based materials, calcium-sodium-phosphate-based materials, as well as many others).

These various orthopedic graft materials, especially the synthetic materials, can be shaped into any number of configurations, including but not limited to blocks, rings, struts, machined shapes, chips, morsels, granules, and so forth.

Furthermore, ceramic cements, such as but not limited to tetracalcium phosphate/tricalcium phosphate cement, calcium sodium phosphate cement, and calcium sulfate, may also be used as orthopedic graft materials. The powder portion would typically be mixed with a citric acid solution or a citrate salt solution in order to form a thick paste which hardens in 5 to 15 minutes.

By the term "orthopedic graft material," as that term is used herein, it is meant any orthopedic material that is capable of either being hydrated and/or rehydrated. By the term "rehydrated," as that term is used herein, it is meant either hydrated and/or rehydrated.

The hydrating and/or rehydrating material may be comprised of any number of aqueous-based liquids, such as water, saline, or the like. Additionally, biologically active materials (e.g., therapeutic and/or prophylactic), such as but not limited to antibiotics, platelet concentrates, bone growth factors, may be introduced into the hydrating and/or rehydrating material, or alternatively, may comprise a portion of, or the entire volume of, the hydrating and/or rehydrating material.

Figure 1:
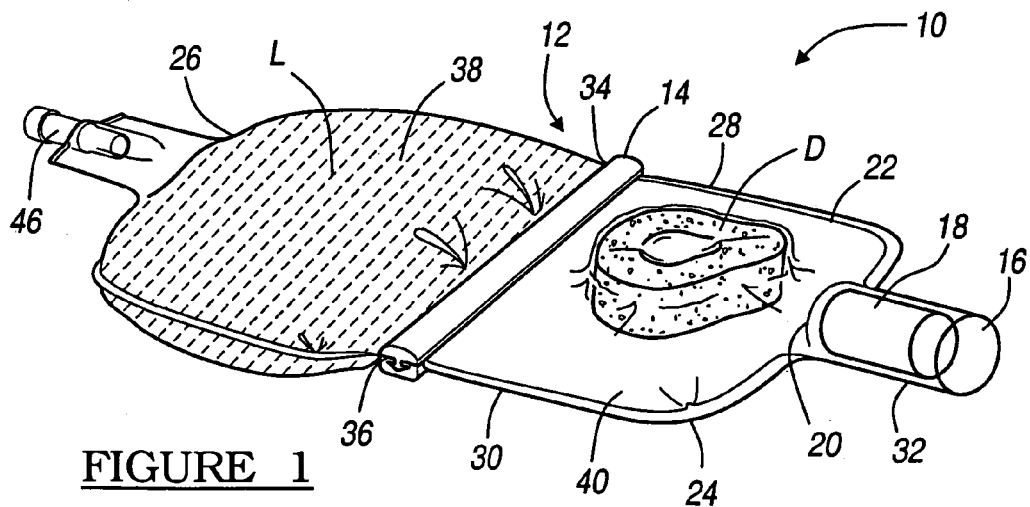
FIG. 1 illustrates a perspective view of a packaging system for orthopedic graft materials, in accordance with one embodiment of the present invention.
Figure 2:
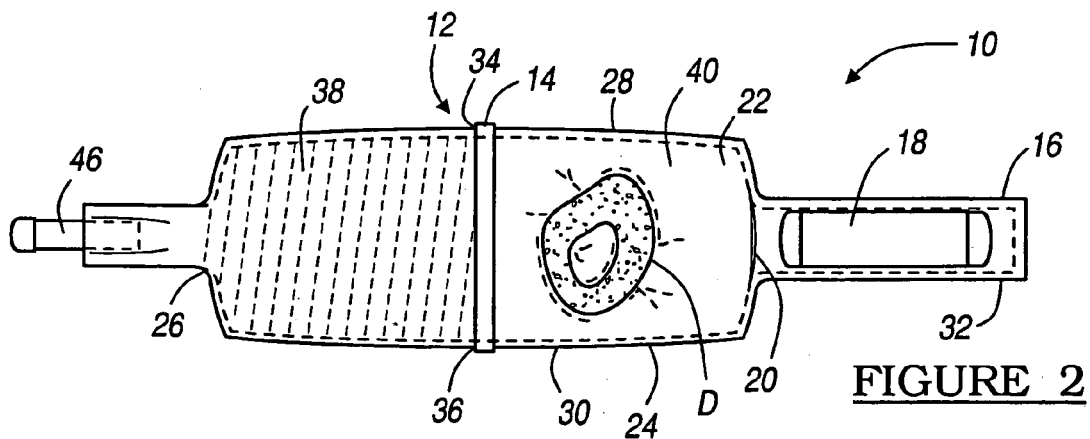
FIG. 2 illustrates a top plan view of a packaging system for orthopedic materials, in accordance with one embodiment of the present invention.
Figure 3:
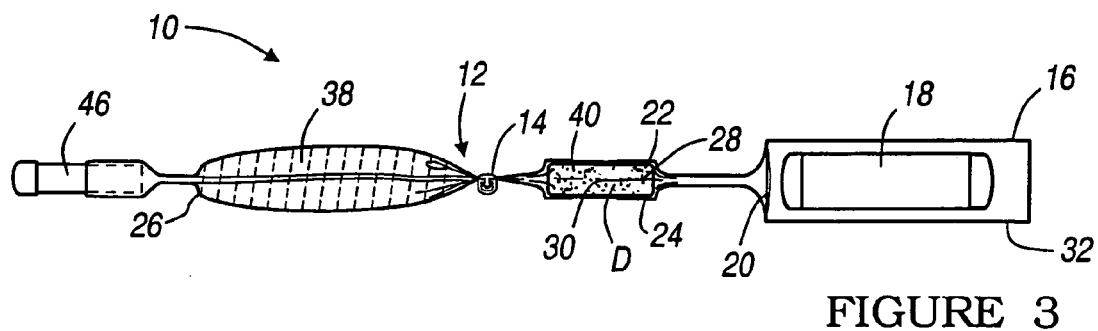
FIG. 3 illustrates a side elevational view of a packaging system for orthopedic materials, in accordance with one embodiment of the present invention.

Referring now to FIGS. 1–3, a packaging system for orthopedic materials is shown designated generally by the reference numeral 10. The packaging system 10 is somewhat similar to the packaging systems described in U.S. Pat. Nos. 5,370,221 and 5,398,483, the entire specifications of which are incorporated herein by reference.

Figure 1A:
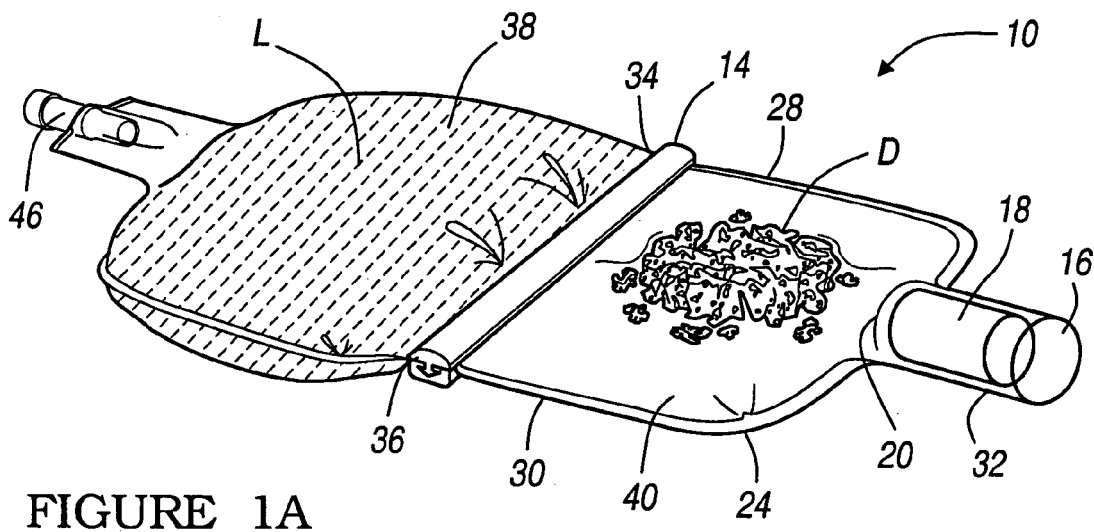
FIG. 1a illustrates a perspective view of a packaging system for morselized orthopedic graft materials, in accordance with one embodiment of the present invention.
Figure 1B:
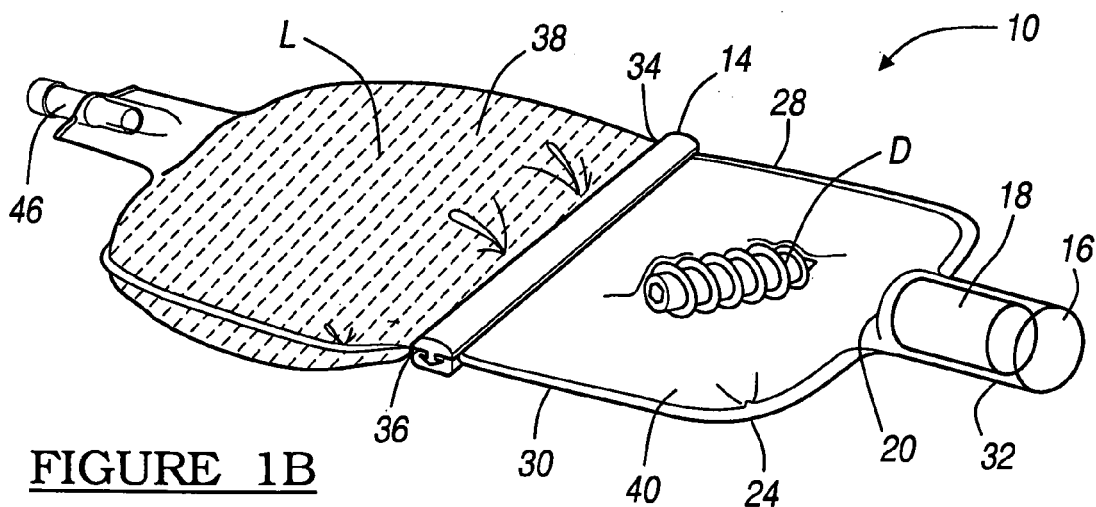
FIG. 1b illustrates a perspective view of a packaging system for machined shape synthetic orthopedic graft materials, in accordance with one embodiment of the present invention.

The packaging system 10 of the present invention primarily includes a preferably flexible container 12, a divider or clamp 14, a tubular portion 16, a vacuum reservoir 18, and an optional gas permeable membrane 20. Preferably, the optional gas permeable membrane 20 is also substantially liquid impermeable. By way of a non-limiting example, the material to be stored can be either substantially solid allograft materials (FIG. 1), morselized allograft materials (FIG. 1a), xenograft materials (not shown), synthetic materials (FIG. 1b), as well as other types of orthopedic graft materials.

The container 12 preferably includes a front panel 22 and a rear panel 24, each made of a thin generally impervious flexible film or laminate. The exact nature of the thin generally impervious flexible film or laminate to be used with the container 12 of the present invention depends upon the nature of the materials to be stored and the conditions under which the materials will be combined and used. For many applications and materials, films and/or laminates of polyethylene, fluoropolymer, nylon, ethyl vinyl alcohol, metal foil, laminated glass and various combinations of the foregoing materials may be used. However, it will be appreciated that other suitable materials may also be used as well.

Additionally, while the container 12 is shown as being substantially rectangular, it is to be understood that the present invention is applicable to flexible containers of other shapes, such as square, triangular or trapezoidal and may have curved edges. The panels 22 and 24 can be formed from a single sheet of flexible film sealed to each other at a bottom edge 26 and side edges 28 and 30.

As noted, the container 12 further includes a tubular portion 16 which is sealed along its continuous edge 32 similar to the edges 26, 28, and 30. Disposed within the tubular portion 16 is the vacuum reservoir device 18, the purpose of which will be more fully explained herein.

The clamp 14 is arranged to provide a temporary seal of the inner surfaces of the panels 20 and 22 to each other along a line extending from an initial point 34 on the sealed edge 28 to a terminal point 36 on the sealed edge 30 to form a first or upper compartment 38 and a second or lower compartment 40. As will be appreciated by those skilled in the art, the clamp 14 is preferably placed on the container 12 prior to being filled with either the liquid component or the orthopedic graft material component.

Figure 4:
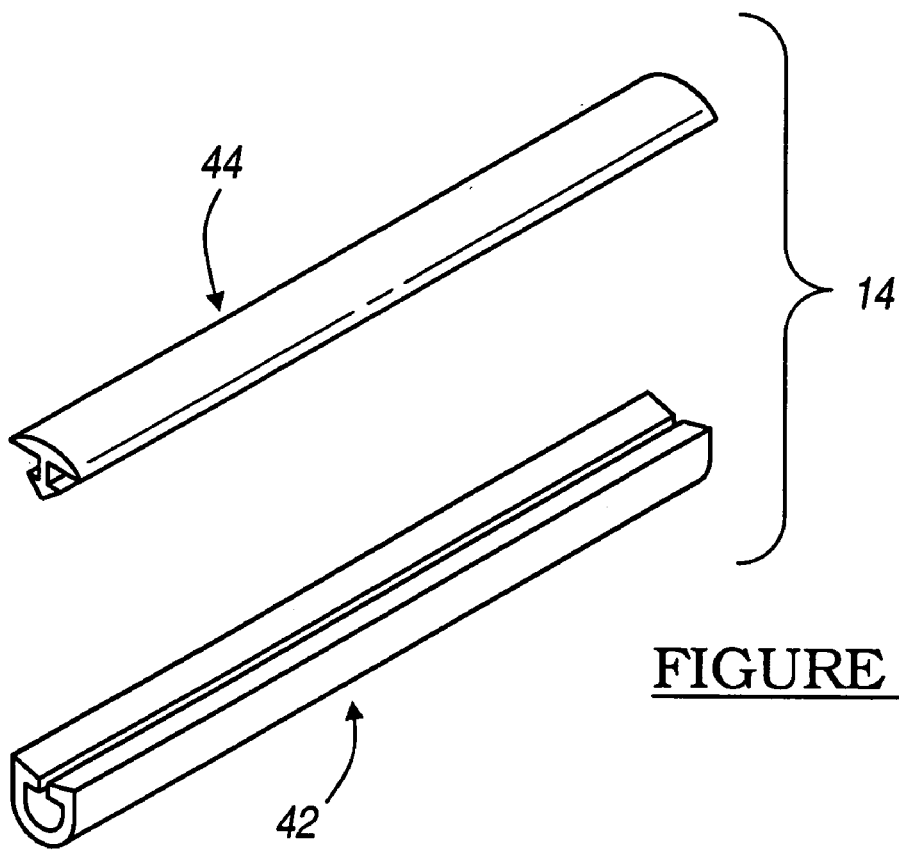
FIG. 4 illustrates an exploded view of a clamp of the packaging system for orthopedic materials, in accordance with one embodiment of the present invention.
Figure 5:
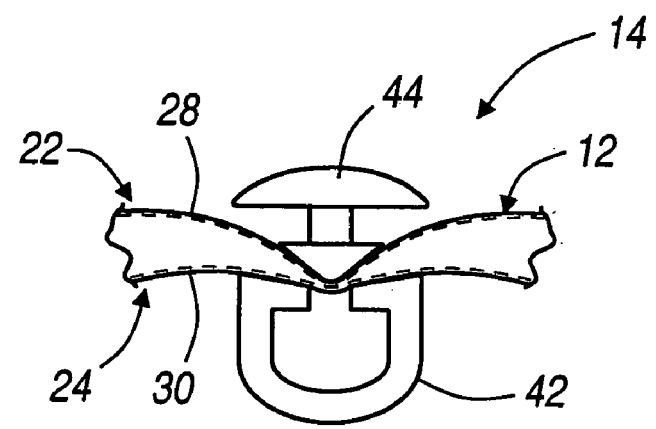
FIG. 5 illustrates a partial cross-sectional view of the clamp of the packaging system for orthopedic materials, in accordance with one embodiment of the present invention.

Referring to FIGS. 4–5, the clamp 14 comprises a C-shaped outer retention member 42 and an I-shaped inner retention member 44 which partially fits within the hollow of the C-shaped outer retention member 42. When the clamp 14 is assembled with respect to the container 12 as shown in FIG. 5, the outer retention member 42 is positioned on the outside of the rear panel 22 and the inner retention member 44 is positioned on the outside of the front panel 20 such that the panels 20 and 22 are pinched together along a pair of parallel lines extending from the initial point 34 to the terminal point 36. The inner retention member 44 has a contoured upper end which fits within the inner hollow of outer retention member 42 and has a thickness substantially equal to the inner distance between the open ends of the C-shaped section of the outside retention member 42 so that a double thickness of panels 20 and 22 is tightly compressed along a pair of parallel lines to form an effective seal or divider. The outer retention member 42 is made of a resilient material so that the inner retention member 44 may be forced into position therein by placing it over the entire length of the opening of the outer retention member 42 and then pressing it into place. Inner retention member 44 has a contoured upper end which can open the open ends of the C-shaped section of the outside retention member 42 to accommodate the inner retention member 44.

The nature of the clamp 14 may also vary. The clamp 14 described in connection with the present invention consisting of an I-shaped inner retention member 44 and a C-shaped outer retention member 42, is preferred because of its simplicity and ease of handling. However, other types of clamps suitable for applying pressure to the container 12 may also be used. In addition, it is possible to replace the clamp 14 with an additional separation seal or divider (not shown). In this embodiment, the separation seal can be either a heat seal or an adhesive seal to separate the upper compartment 38 from the lower compartment 40. The strength of this separation seal must be such that it can be broken by placing pressure on either of the compartments 38 and 40 without damaging the panels 20 and 22. This separation seal may also be used in conjunction with the clamp 14.

Figure 6:
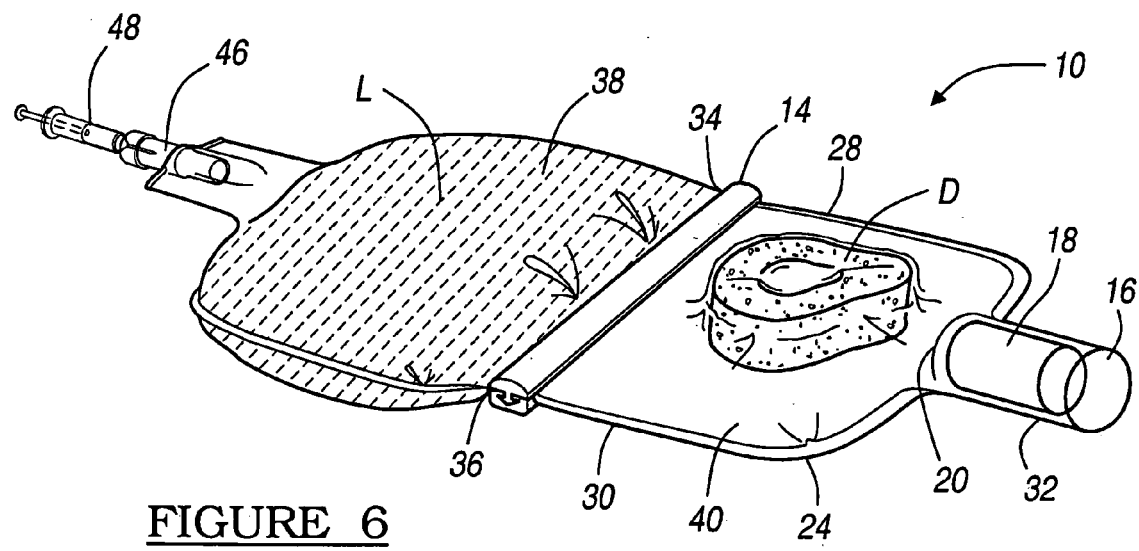
FIG. 6 illustrates a perspective view of a material introduction device and the packaging system for orthopedic materials, in accordance with one embodiment of the present invention.

The method of packaging the components of the orthopedic graft materials within the packaging 12 will now be described. The side edges 26 and 28 of the front panel 20 and the rear panel 22 are typically secured together by heat sealing, although other means of sealing may be used as well, such as adhesives. The clamp 14 is then placed over the front panel 20 and the rear panel 22 so as to form a temporary seal between the front panel 20 and the rear panel 22 and partially form the upper compartment 38 and the lower compartment 40 under environmentally controlled conditions. In certain circumstances, it will be necessary to position the orthopedic graft material D within the lower compartment 40 prior to heat sealing of the respective edges of the lower compartment 40 due, in part, to the size and configuration of the orthopedic graft material. In that circumstance, once the orthopedic graft material D is properly positioned, a heat seal then closes the lower compartment 40. The container 12 is then sterilized employing gamma radiation, electron beam or other means. The liquid component L (e.g., water, saline, or the like) is then filled into the upper compartment 38 under aseptic conditions and then the upper compartment 38 is closed by the seal 24. However, it should be noted that it is not necessary that the liquid component L be added at the same time the orthopedic graft material D is introduced. For example, the liquid component L can be introduced immediately before the infusion process is to take place, for example, in the operating room. Additionally, a port device 46 may be provided on the upper compartment 38 in order to introduce additional materials into the liquid component L (via syringe 48), such as but not limited to biologically active materials, as shown in FIG. 6. Preferably, the port device 46 is self-sealing, or is provided with a cap or similar device, so as to prevent any leakage problems.

The main benefit of the present invention is that it provides a system for in situ mixing of the two components to produce a rehydrated orthopedic graft material. This is achieved by maintaining the lower compartment 40 under vacuum. This vacuum condition is facilitated by the presence of the vacuum reservoir 18 in the tubular portion 16. The vacuum reservoir 18 preferably has a sufficiently large volume to take up the residual gases which will be replaced in the interstitial voids between the particles of the orthopedic graft material by the liquid component upon release or breaking of the seal between the first and second compartments. The purpose of the optional gas permeable membrane 20 is to allow air to be drawn out of the lower compartment 40 (e.g., during the creation of the vacuum condition), while preventing any liquid or particulate matter from penetrating into the tubular portion 16 or leaving the graft material.

Figure 7:
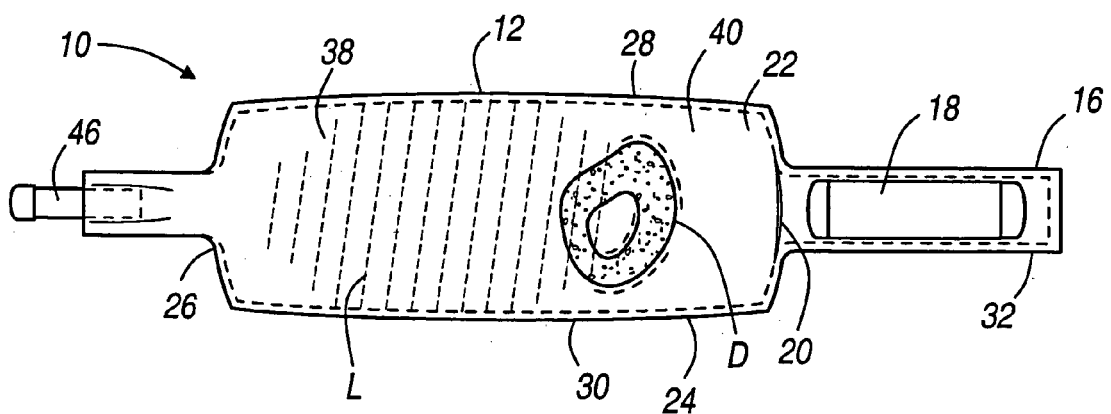
FIG. 7 illustrates a top plan view of the initial infusion process of the dehydrated orthopedic graft material, in accordance with one embodiment of the present invention.
Figure 8:
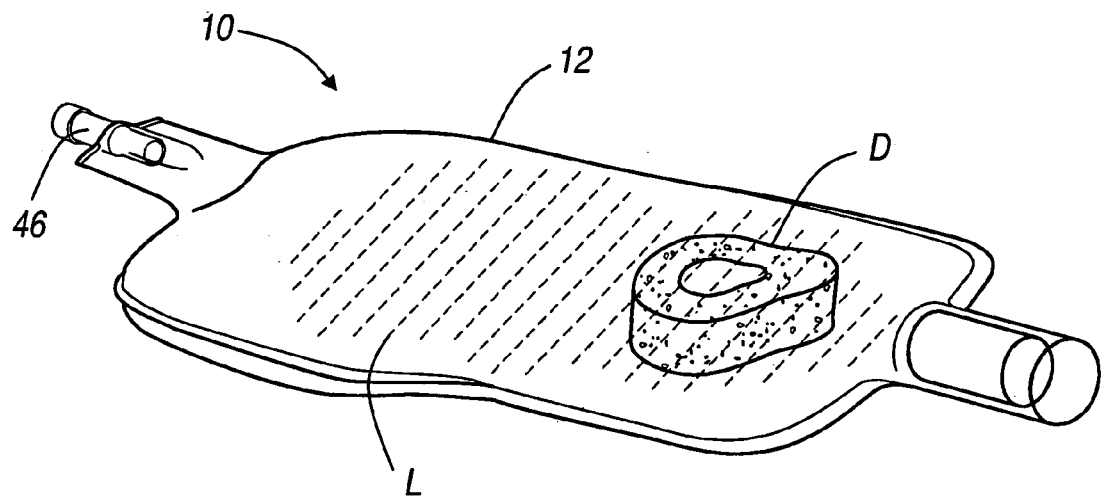
FIG. 8 illustrates a perspective view of the initial infusion process of the dehydrated orthopedic graft material, in accordance with one embodiment of the present invention.
Figure 9:
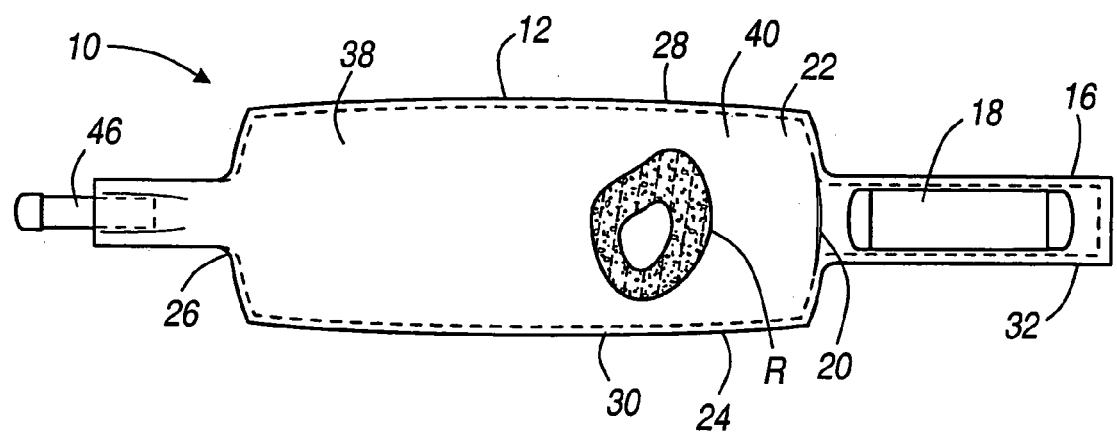
FIG. 9 illustrates a top plan view of the completion of the infusion process of the dehydrated orthopedic graft material, in accordance with one embodiment of the present invention.
Figure 10:
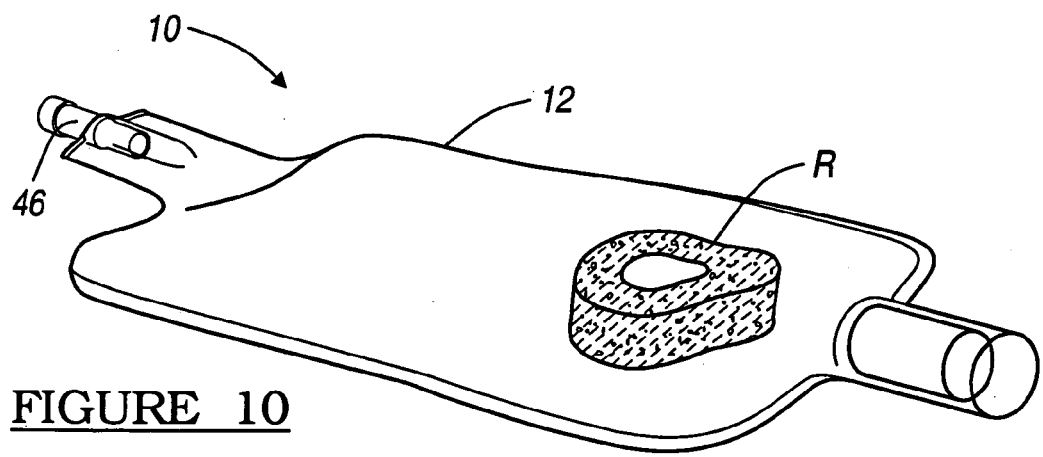
FIG. 10 illustrates a perspective view of the completion of the infusion process of the dehydrated orthopedic graft material, in accordance with one embodiment of the present invention.
Figure 11:
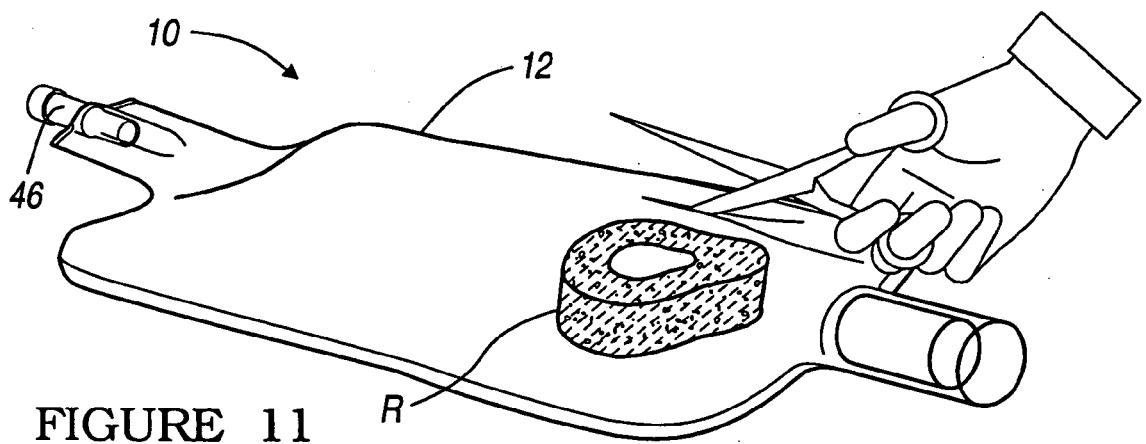
FIG. 11 illustrates a perspective view of the opening of the packaging system for orthopedic materials, in accordance with one embodiment of the present invention.
Figure 12:
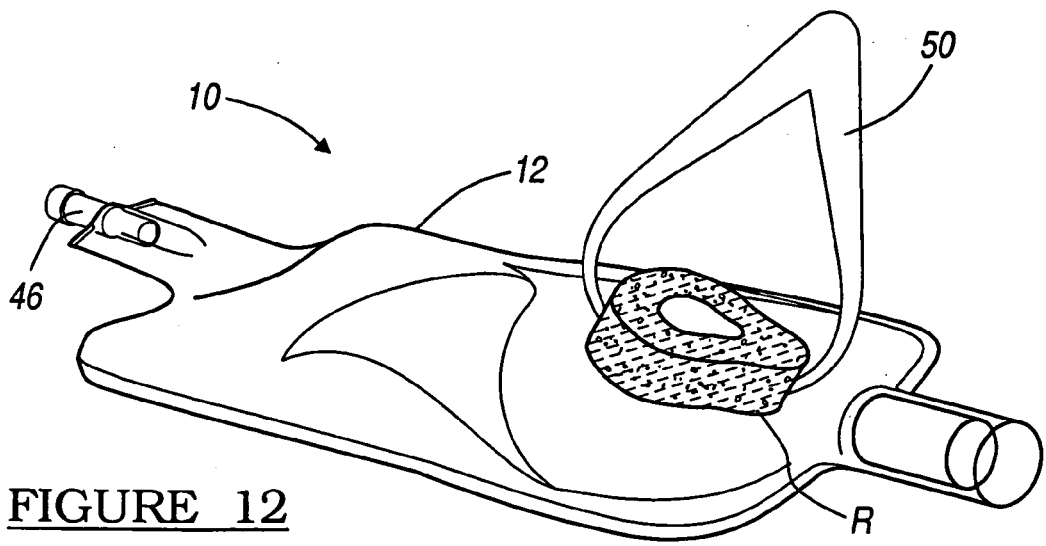
FIG. 12 illustrates a perspective view of the rehydrated orthopedic graft material being removed from the packaging system for orthopedic materials, in accordance with one embodiment of the present invention.

The force which transfers the liquid component L into the second compartment 40 to combine with the orthopedic graft material component D is thus the pressure differential between the atmospheric pressure acting on the walls of the first compartment 38 and the pressure prevailing in the second compartment 40. The function of the vacuum reservoir 18 is to maintain a sufficiently low pressure in the second compartment 40 until the orthopedic graft material component D has been completely and thoroughly infused by the liquid component L. Once the clamp 14 has been removed, the liquid component L will rapidly flow into the second compartment 40, completely and thoroughly infusing the orthopedic graft material component D, as shown in FIGS. 7–8. Once the infusion process is complete, the hydrated (or rehydrated) orthopedic graft material R will be ready for immediate implantation, as shown in FIGS. 9–10 Following the infusion process, the container 12 holding the hydrated/rehydrated orthopedic graft material R is opened (see FIG. 11) and the hydrated/rehydrated graft material R is removed (see FIG. 12), preferably with a sterile instrument such as a forceps 50, and is now ready for immediate affixation onto a bone defect, for example.

Figure 13:
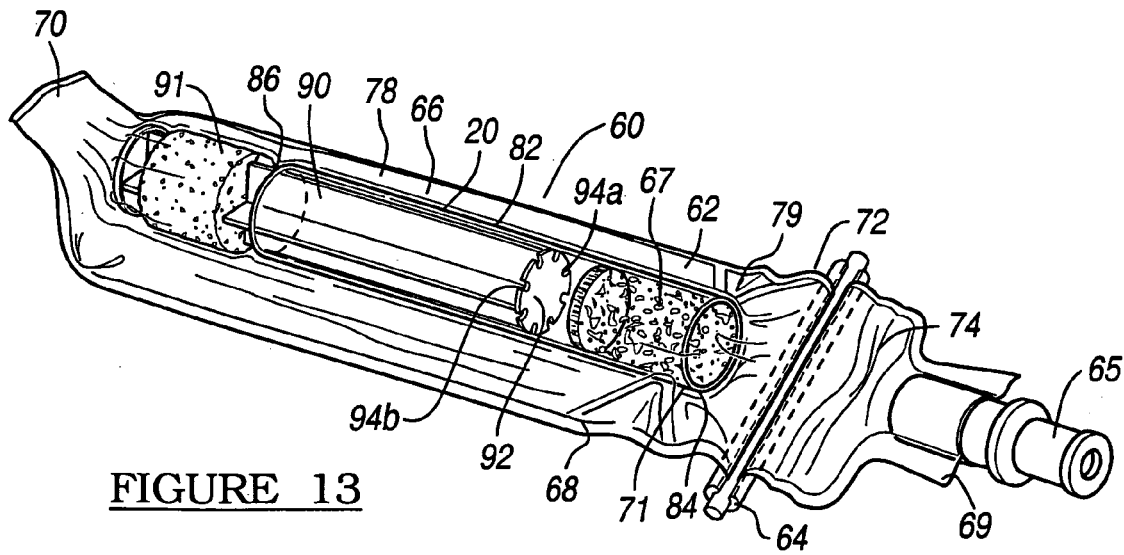
FIG. 13 represents a perspective view of a packaging system for an orthopedic graft material in accordance with another embodiment of the invention.
Figure 14:
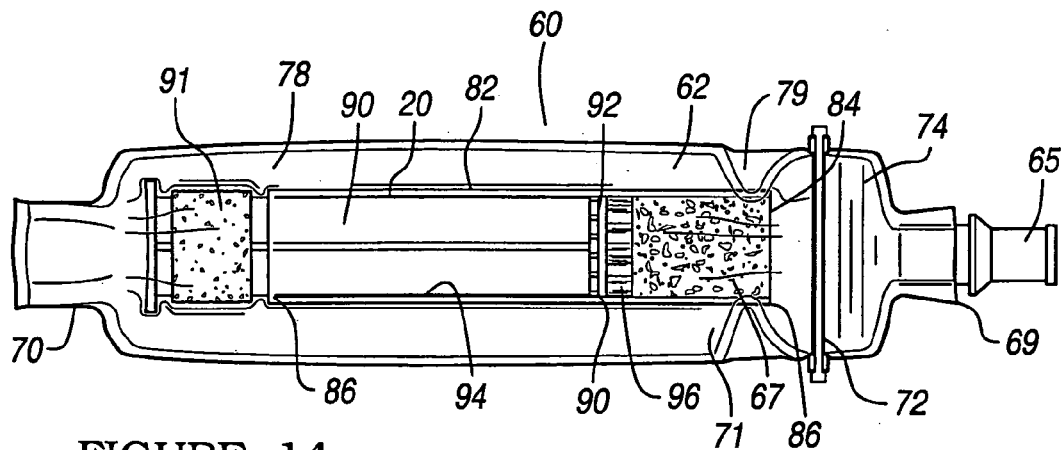
FIG. 14 represents a top view of the packaging system shown in FIG. 13.
Figure 15:
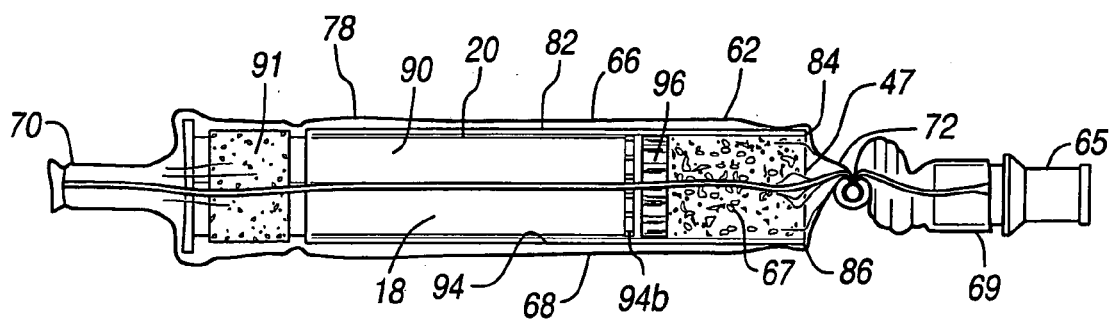
FIG. 15 represents a side view of a packaging system shown in FIG. 13.

Referring to FIGS. 13–15, a packaging system for orthopedic materials is shown designated generally by the reference numeral 60. The packaging system 60 of the present embodiment includes a flexible container 62, a divider or clamp 64, and a tubular port 65. Disposed within the flexible container is a syringe 20 containing biocompatible material 67 of morselized allograph materials, xenograft materials, synthetic bone cement, or any other types of orthopedic graft materials.

The container 62 contains a front panel 66 and a rear panel 68. The exact nature of the layers 66 and 68 depend upon the nature of the materials to be stored and the nature of the environmental conditions the system 60 will be subject to. The container 62 further defines a proximal end 69 and a distal end 70. Disposed between the proximal end and distal ends 69 and 70 at a medial location 72 is the clamp 64 which functions as described above. Defined between the clamp 64 and the proximal end 68 is a first cavity 74 which is configured to hold reconstitution liquid 76. Disposed between the clamp and a distal end 70 is a second cavity 78 which holds the syringe 20.

The second cavity 78 can optionally have a first portion 79 adjacent to the medial location 72 having a radius which comports to the outer diameter 71 of the syringe. In this regard, as described below, a body portion 82 of the syringe 20 functions to act as a fluid couple between the first cavity 74 and the second cavity 78.

The body 82 further acts as a vacuum reservoir 18 which obviates the need for a separate vacuum holding component. The first portion 79 functions to seal the syringe 20 to an internal surface of the container 62. The vacuum reservoir 18 of the syringe 20 functions to provide a vacuum sufficient enough to remove any residual gases within the orthopedic material 67 or the reconstitution liquid. Disposed at a proximal end 84 of the generally cylindrical body 82 is the orthopedic material 67. Disposed in the aperture 86 formed by the distal end 88 of the cylindrical body 82 is a plunger 90. The plunger 90 has a cylindrical portion 92 which comports to an interior surface 94 of the cylindrical body 82 and further defines a plurality of through passages 94a–94e, which function to allow gases to pass through the orthopedic material 67 into the second cavity 78. Optionally, the plunger has a locking device 91 which functions to resist the movement of the plunger 90 during the reconstitution of the orthopedic material 67. This locking device 91 can take the form of foam or a releasable polymeric clasp.

Disposed between the plunger 90 and the orthopedic material 67 is a layer of gas permeable material 96 which functions to allow the air to flow through and out of the orthopedic material 67 into the second cavity 78 and into the vacuum reservoir device 18 as previously described. Further, the gas permeable material 96 functions to prevent the reconstitution liquid from being drawn out of the orthopedic material or entering the body of the syringe 20. Optionally, a second gas and reconstitution liquid permeable membrane 97 can be disposed at the proximal end 84 of the syringe 20 so as to hold the orthographic material in the syringe 20.

The force needed to transfer the liquid into the syringe 20 to combine with the orthopedic material 67 is the difference between the atmospheric pressure acting on the first cavity 74 and the pressure within the cavity 78. As previously described, the function of the vacuum reservoir 10 within the syringe 20 is to maintain a sufficiently low pressure in the second cavity 78 so as to allow the proper amount of liquid to be pulled into the orthopedic material 67 in the syringe 20.

Figure 16:
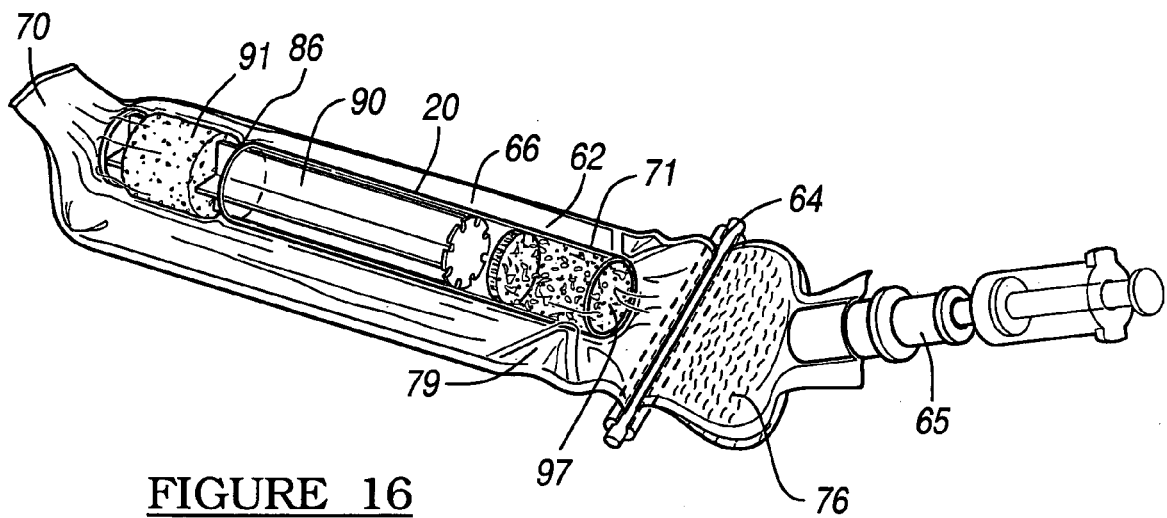
FIG. 16 represents a perspective view of the introduction of reconstitution liquid into the packaging system shown in FIG. 13.
Figure 17:
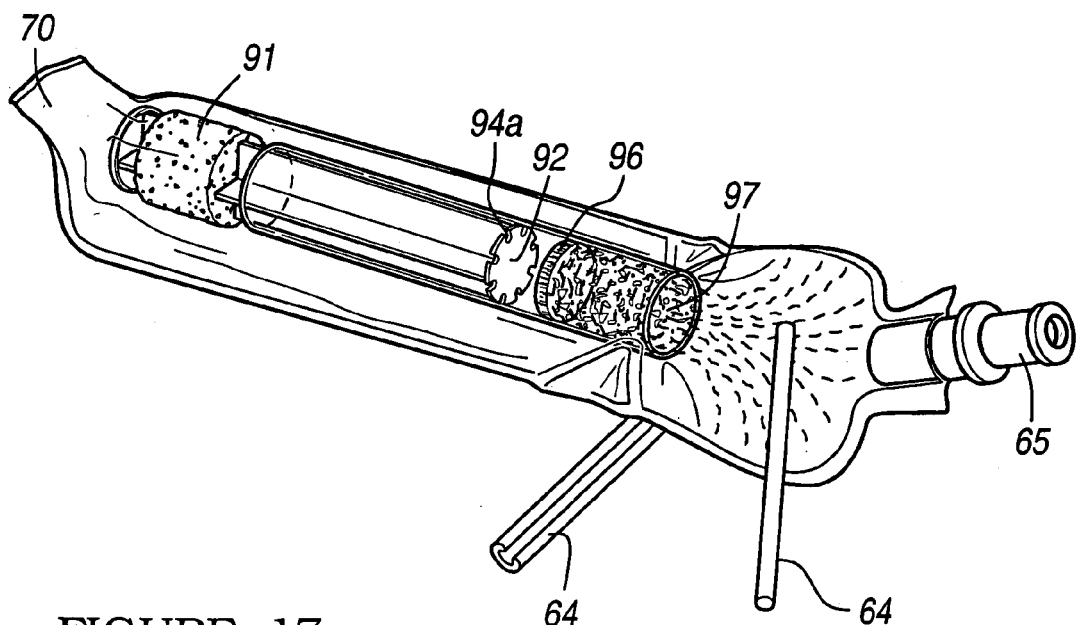
FIG. 17 represents a perspective view of the initial infusion process of the rehydration of the allograph material in accordance with one embodiment of the present invention.
Figure 18:
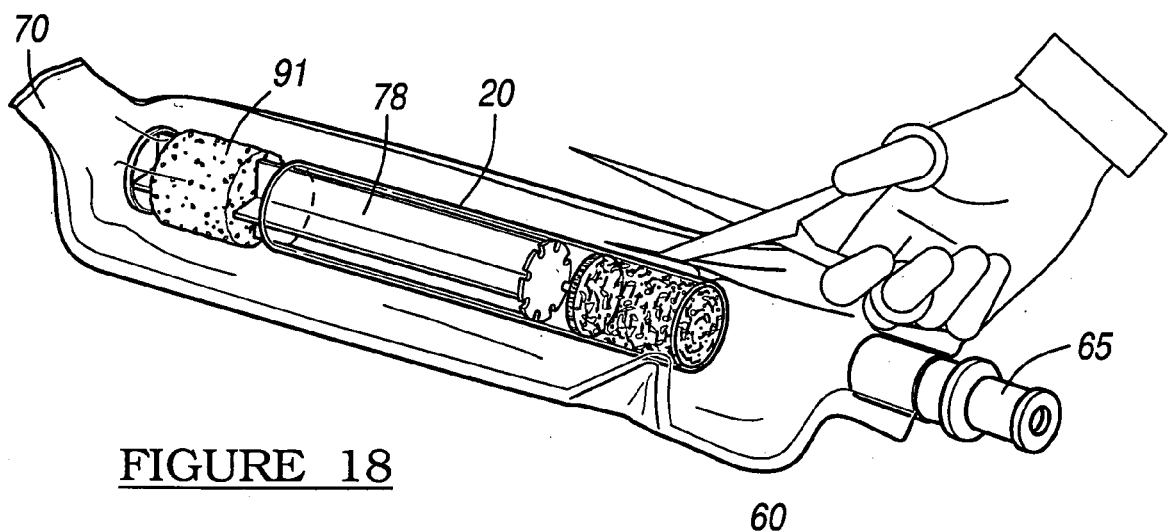
FIG. 18 represents a perspective view of the opening of the packaging system shown in FIG. 13.
Figure 19:
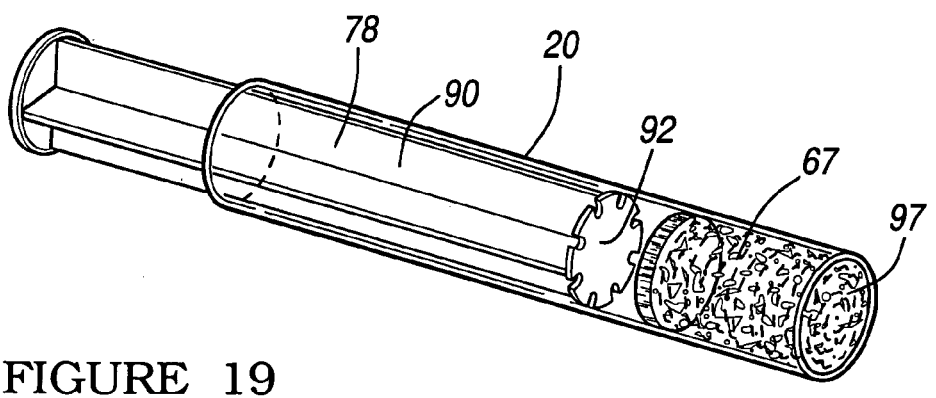
FIG. 19 represents a perspective view of a syringe shown in FIG. 1 having reconstitution bone allograph material.

The infusion of the orthopedic material 67 is shown in FIGS. 16 and 17. It should be noted that the first cavity 74 can either be prepackaged with reconstitution fluid 76, or can have the reconstitution fluid 76 injected through the port 65. The use of the clamp 64 allows the mixing of various biological material such as platelets or antibiotics into the reconstitution liquid 76 prior to infusion. It additionally is envisioned that the reconstitution liquid can be injected directly into the port 65 without the use of the clamp 64 for direct rehydration of the material 67. Once rehyrdration is complete, the orthopedic material 67 is ready for implantation. As is shown in FIG. 18, the syringe is removed from the container 62. The locking device 91 is removed from the plunger 90. The plunger 90 can now be used to implant the orthopedic material 67 or bone cement material as is needed. It is envisioned that injection heads (not shown) can be coupled to the syringe 20 to assist in the interoperative use of the orthopedic material 67 or the bone cement.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. A system for storing orthopedic graft material, comprising:
   a container defining a first cavity capable of receiving a liquid;
   a syringe having a movable plunger and a body which is configured to be a vacuum reservoir and to hold orthopedic material, said syringe being disposed within the first cavity; and
   a mechanism configured to restrict movement of the plunger to substantially retain a vacuum in the syringe, wherein the container defines a second cavity configured to receive the liquid and a coupling portion defined between the first and second cavities.

2. The system of claim 1, further comprising a clamp between the first and second cavities.

3. The system according to claim 1, wherein the syringe is at least partially disposed within a fluid couple.

4. The system of claim 3, wherein an interface between said syringe and said fluid couple is substantially sealed and wherein said body defines a fluid passage between said first and second cavities.

5. The system according to claim 1, wherein the plunger defines at least one through passage.

6. The system of claim 1, further comprising a gas permeable membrane between said plunger and the orthopedic material.

7. The system according to claim 1, wherein the first cavity comprises reconstitution liquid.

8. The system according to claim 7, wherein said reconstitution liquid selected from the group consisting of water, saline, biologically active materials, platelets, antibiotics, and combinations thereof.

9. A system for storing orthopedic graft material, comprising:
   a container defining a first cavity capable of receiving a liquid; and
   a syringe having a body which is configured to be a vacuum reservoir and to hold orthopedic material, said syringe being disposed within the first cavity further comprising a gas permeable membrane between a plunger and the orthopedic material, wherein the gas permeable membrane allows the passage of gaseous fluids but restricts the flow of fluids therethrough.

10. A container for the storing and reconstitution of orthopedic implant materials with a liquid comprising:
   a dividing device to divide the container into first and second cavities, the first cavity containing the liquid and the second cavity comprising a syringe holding the orthopedic material under a vacuum, said syringe further defining a vacuum reservoir fluidly coupled to the second cavity.

11. The container according to claim 10, wherein the syringe comprises a body which is fluidly disposed between and fluidly couples the first and second cavities.

12. The container according to claim 11, wherein the body defines a vacuum storage device.

13. The container according to claim 10, further comprising a gas permeable membrane disposed within the syringe.

14. The container according to claim 10, wherein the syringe comprises a plunger which defines a plurality of through passages.

15. The container according to claim 10, wherein the container defines a seal around an outer surface of the syringe.

16. The container according to claim 10, further comprising an injection port fluidly coupled to the first cavity to receive the liquid.

* * * * *